United States Patent [19]

Maywald et al.

[11] Patent Number: 5,264,580

[45] Date of Patent: Nov. 23, 1993

[54] PREPARATION OF ISOXAZOLE-3,4-DICARBOXYLIC ACID DERIVATIVES

[75] Inventors: Volker Maywald, Ludwigshafen; Thomas Kuekenhoehner, Boehl-Iggelheim; Peter Muenster, Neulussheim; Stefan Stahl, Worms, all of Fed. Rep. of Germany

[73] Assignee: BASF Aktiengesellschaft, Ludwigshafen, Fed. Rep. of Germany

[21] Appl. No.: 39,573

[22] Filed: Mar. 23, 1993

[30] Foreign Application Priority Data

Mar. 26, 1992 [DE] Fed. Rep. of Germany ....... 4209848

[51] Int. Cl.$^5$ ............................................. C97D 261/08
[52] U.S. Cl. ................................................. 548/248
[58] Field of Search ..................................... 548/248

[56] References Cited

U.S. PATENT DOCUMENTS 3,502,660  3/1970  Butler et al. ................. 260/240
3,699,117 10/1972  Butler et al. ................. 260/307.5

FOREIGN PATENT DOCUMENTS 3931627  9/1989  Fed. Rep. of Germany ...... 548/248

OTHER PUBLICATIONS

L. Panizzi, Gazz. Chim Ital., 69 (1939) 322ff; 43, pp. 322-325.
V. Spiro, E. Aiello and A. Mazza, Ann. Chimica 57 (1967) No. 7, 836-845.

*Primary Examiner*—Mary Lee
*Assistant Examiner*—Joseph K. McKane
*Attorney, Agent, or Firm*—Keil & Weinkauf

[57] ABSTRACT

A process for preparing isoxazole-3,4-dicarboxylic acid derivatives of the formula I

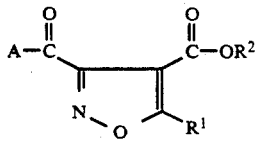

where
$R^1$ is hydrogen, alkyl, cycloalkyl or phenyl, or a 5- to 6-membered heterocyclic radical, and the organic radicals can have substituents which are inert under the reaction conditions;
$R^2$ is hydrogen, alkyl, cycloalkyl, benzyl or $C_3$-$C_6$-alkenyl;
A is $NR^3R^4$ where $R^3$ is hydrogen or an aliphatic or cycloaliphatic radical and $R^4$ is an aliphatic or cycloaliphatic radical or unsubstituted or substituted phenyl, or $R^3$ forms together with $R^4$ a 4- to 7-membered alkylene chain which can be interrupted by oxygen, sulfur or N-methyl, or is $OR^5$ where $R^5$ is alkyl, cycloalkyl, benzyl or alkenyl;
by deprotonation of a CH-acid compound of the formula II

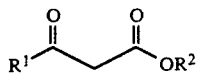

using a base and reacting with hydroximyl chlorides of the formula III

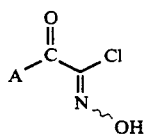

wherein a magnesium alcoholate of the formula IV

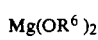

where $R^6$ is an aliphatic or cycloaliphatic radical is used for the deprotonation.

5 Claims, No Drawings

PREPARATION OF ISOXAZOLE-3,4-DICARBOXYLIC ACID DERIVATIVES

The present invention relates to a process for preparing isoxazole-3,4-dicarboxylic acid derivatives of the formula I

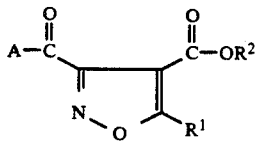

where
- $R^1$ is hydrogen, alkyl, cycloalkyl or phenyl, or a 5- to 6-membered heterocyclic radical, and the organic radicals can have substituents which are inert under the reaction conditions;
- $R^2$ is hydrogen, alkyl, cycloalkyl, benzyl or $C_3$-$C_6$-alkenyl;
- A is $NR^3R^4$ where $R^3$ is hydrogen or an aliphatic or cycloaliphatic radical and $R^4$ is an aliphatic or cycloaliphatic radical or unsubstituted or substituted phenyl, or $R^3$ forms together with $R^4$ a 4- to 7-membered alkylene chain which can be interrupted by oxygen, sulfur or N-methyl, or is $OR^5$ where $R^5$ is alkyl, cycloalkyl, benzyl or alkenyl;

by deprotonation of a CH-acid compound of the formula II

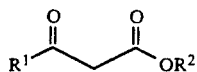

using a base and reacting with hydroximyl chlorides of the formula III

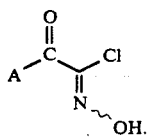

Direct synthesis of 3-carbamoylisoxazole-4-carboxylic acid derivatives Ia

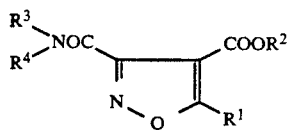

by base-induced reaction of β-keto esters or acids II with hydroximyl chlorides of the formula IIIa

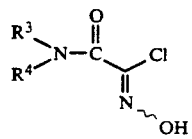

is not described in the literature.

On the other hand, the base-induced reaction of β-keto esters with hydroximyl chlorides of the formula IIIb

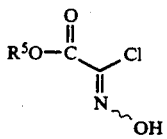

where $R^5$ is methyl or ethyl is disclosed in the literature (L. Panizzi, Gazz. Chim Ital., 69 (1939) 322ff; V. Spiro, E. Aiello and A. Mazza, Ann. Chimica 57 (1967) No. 7 836–845; V. Maywald et al., DE-A-39 31 627) as is the reaction of alkyl γ,γ-diethoxyacetoacetates with hydroximyl chlorides of the formula IIIb where $R^5$ is alkyl or benzyl (K. Butler; L. H. Conover, R. B. Woodward, U.S. Pat. No. 3,699,117). However, in these processes either sodium alcoholates or sodium hydride are used as base to convert the β-keto ester into the enolate. The products Ib

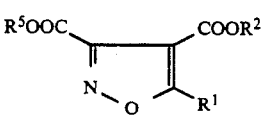

are obtainable by these processes usually only in low yields, however.

It is an object of the present invention to find a maximally simple and economic process for synthesizing the compounds Ia and Ib, which are used as intermediates for organic syntheses, especially for preparing crop protection agents (cf. DE-A 39 31 627).

We have found that this object is achieved by a process for preparing isoxazole-3,4-dicarboxylic acid derivatives of the formula I

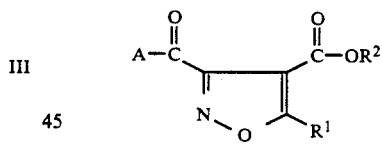

in which the substituents have the meanings defined at the outset, by deprotonation of a CH-acid compound of the formula II

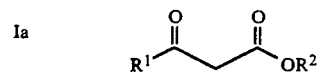

using a base and reacting the anion with hydroximyl chlorides of the formula III

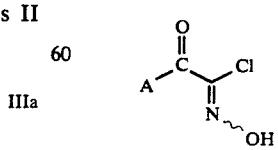

wherein a magnesium alcoholate of the formula IV

$$Mg(OR^6)_2 \quad\quad IV$$

where $R^6$ is an aliphatic or cycloaliphatic radical is used for the deprotonation.

Suitable aliphatic radicals for $R^6$ are unsubstituted or substituted alkyl or alkenyl. Examples are $C_1$-$C_6$-alkyl, especially $C_1$-$C_4$-alkyl such as methyl, ethyl, propyl, isopropyl, butyl, isobutyl, sec-butyl and tertbutyl, which can be substituted once by $C_1$-$C_4$-alkoxy such as methoxy, ethoxy, propoxy, isopropoxy, butoxy, isobutoxy, sec-butoxy or tert-butoxy, especially methoxy and ethoxy, $C_1$-$C_4$-alkylthio such as methylthio, ethylthio, propylthio, isopropylthio, butylthio, isobutylthio, sec-butylthio or tert-butylthio, especially methylthio and ethylthio, halogen as mentioned for $R^1$, especially fluorine and chlorine, $C_3$-$C_6$-cycloalkyl as mentioned for $R^1$, especially cyclopropyl, cyano or phenyl; $C_3$-$C_6$-alkenyl, especially $C_3$-$C_5$-alkenyl such as 2-propenyl, 1-methyl-2-propenyl or 1,1-dimethyl-2-propenyl. Examples of cycloaliphatic radicals are cyclopentyl and cyclohexyl.

The yields achieved on use of magnesium alcoholates as base were, surprisingly, far higher than in processes disclosed in the literature, which give yields of only 14 to 44% on use of sodium alcoholates or 21 to 63% on use of sodium hydride, as is shown by the compilation in Table I.

TABLE I

| $R^1$ | $R^5$ | $R^2$ | Base | Solvent | Yield | Reference |
|---|---|---|---|---|---|---|
| Me | Et | Et | NaOMe | MeOH | 44% | 1) |
| Me | Me | Me | NaOMe | MeOH | 38% | 2) |
| Me | Me | Et | NaH | Toluene | 63% | 3) |
| Me | Me | Me | NaH | Benzene | 48% | 3) |
| Me | Me | Me | NaH | Toluene | 46% | 3) |
| Et | Me | Me | NaH | Toluene | 21% | 3) |
| iPr | Me | Me | NaH | Toluene | 31% | 3) |
| iPr | Me | Me | NaH | Benzene | 28% | 3) |
| iPr | Me | Et | NaH | Toluene | 32% | 3) |
| iPr | Me | Me | NaOMe | MeOH | 18% | 2) |
| iPr | Me | Me | NaOMe | THF | 14% | 2) |
| process according to the invention | | | | | | |
| iPr | Me | Me | Mg(OMe)$_2$ | THF | 74% | |
| iPR | Me | Et | Mg(OEt)$_2$ | THF | 78% | |
| iPr | Me | Et | Mg(OEt)$_2$ | Toluene | 69% | |

THF = tetrahydrofuran
Me = methyl; Et = ethyl; i-Pr = isopropyl
1) L. Panizzi, Gazz. Chim. Ital., 69 (1939) 322;
2) carried out in a similar manner to ref. 1
3) V. Maywald et al., DE-A-39 31 627

Suitable magnesium alcoholates are those of $C_1$-$C_6$-alcohols such as methanol, ethanol, n-propanol, isopropanol, n-butanol, isobutanol, n-pentanol, isopentanol, n-hexanol or isohexanol, and of $C_3$-$C_6$-alkenols such as allyl alcohol and cycloalkyl alcohols such as cyclopentanol and cyclohexanol.

Readily obtainable and low-cost magnesium alcoholates such as magnesium methylate, ethylate or propylate, which are commercially available, are particularly preferred.

Processes for preparing alkaline earth metal alcoholates are disclosed in the literature (see Houben-Weyl, Methoden der Organischen Chemie, 4th edition, Volume VI/2, Oxygen Compounds I, page 15, Georg Thieme Verlag).

The reaction according to the invention is preferably carried out by converting the $\beta$-keto acid or the $\beta$-keto ester II into the magnesium enolate with 1-5 times, preferably 1-2 times, the molar amount of the magnesium alcoholate IV in an inert organic solvent at from −20° C. to the boiling point of the solvent, preferably at from 0° C. to 50° C. This is preferably carried out by introducing the magnesium alcoholate IV into the solvent and adding a solution of the starting material II to this mixture. Subsequently the hydroximyl chloride IIIa or IIIb is added dropwise at from 0° C. to the boiling point of the solvent, preferably at 20°-70° C. In order to prevent the formation of furoxanes, which may be produced by dimerization of the hydroximyl chlorides III or their secondary products, the addition should take place slowly, ie. over the course of 1-12 hours, preferably 3-8 hours, to keep the concentration low.

Suitable organic solvents are very generally hydrocarbons such as pentane, hexane, heptane, petroleum ether, naphtha or cyclohexane, halohydrocarbons such as dichloromethane, tetrachloromethane and chlorobenzene, nitriles such as acetonitrile, butyronitrile and benzonitrile, amides such as formamide, methylformamide, dimethylformamide and diethylformamide, sulfoxides and sulfones such as dimethyl sulfoxide and sulfolane. Particularly suitable are ethers such as diethyl ether, ethyl n-propyl ether, di-n-butyl ether, diisoamyl ether, cyclohexyl methyl ether, methyl tert-butyl ether, diisopropyl ether, ethylene glycol dimethyl ether, diethylene glycol dimethyl ether, tetrahydrofuran, dioxane, anisole, phenetole or aromatic hydrocarbons such as benzene, toluene or xylene. It is, of course, also possible to use mixtures of these solvents.

The amount of solvent is not critical and is normally 1-20 times, preferably 1-10 times, the weight of the $\beta$-keto acid or $\beta$-keto ester II.

After the reaction is complete (after about 1-24 hours), the solution is acidified with a suitable acid, and the reaction mixture is refluxed for 1-6 hours. It may be advantageous to remove the water which is produced in the cyclization from the reaction mixture. Expediently used for this in the case of water-immiscible solvents is a water separator, and in the case of water-miscible solvents a Soxhlet extractor whose extraction thimble is filled with a suitable desiccant, for example molecular sieve. The reaction product I can then be isolated in a conventional way by adding water and subsequently extracting with an organic solvent.

Acids which are expediently used are carboxylic and sulfonic acids such as formic acid, acetic acid, propionic acid, oxalic acid, methanesulfonic acid or p-toluenesulfonic acid, inorganic acids such as sulfuric acid, hydrochloric acid, phosphoric acid and salts such as ammonium chloride and amine hydrochlorides.

No special pressure conditions are necessary, and the reaction is generally carried out under atmospheric pressure.

The process can be carried out either continuously or batchwise. As an example of a continuous process, reaction in a tubular reactor may be mentioned.

With a view to the intended use of the intermediates I, the substituents $R^1$, $R^2$ and A have the following meanings, in particular:

$R^1$ hydrogen;
a lower alkyl radical such as $C_1$-$C_6$-alkyl, in particular $C_1$-$C_4$-alkyl such as methyl, ethyl, propyl, isopropyl, butyl, isobutyl, sec-butyl or tert-butyl, which can be substituted by one to three halogens such as fluorine, chlorine, bromine or iodine, in particular fluorine and chlorine, a $C_1$-$C_3$-alkoxy such as methoxy, ethoxy, propoxy and isopropoxy, especially methoxy and ethoxy, or a $C_3$-$C_6$-cycloalkyl such as cyclopropyl, cyclobutyl, cyclopentyl and cyclohexyl, especially cyclopropyl;
cycloalkyl such as $C_3$-$C_8$-cycloalkyl, eg. cyclopropyl, cyclobutyl, cyclopentyl, cyclohexyl, cycloheptyl and cyclooctyl, especially cyclopropyl, which can be substituted one to three times by $C_1$-$C_4$-alkyl as mentioned above, especially methyl; a 5- to 6-membered saturated, unsaturated or aromatic heterocyclic radical containing one or two hetero atoms selected from the group comprising oxygen, sulfur and nitrogen, such as 2-tetrahydrofuranyl, 3-tetrahydrofuranyl, 2-tetrahydrothienyl, 3-tetrahydrothienyl, 2-tetrahydropyranyl, 3-tetrahydropyranyl, 4-tetrahydropyranyl, 2-furanyl, 3-furanyl, 2-thienyl, 3-thienyl, 3-isoxazolyl, 4-isoxazolyl, 5-isoxazolyl, 2-oxazolyl, 4-oxazolyl, 5-oxazolyl, 2-thiazolyl, 4-thiazolyl, 5-thiazolyl, 2-pyridyl, 3-pyridyl or 4-pyridyl, which can be substituted by $C_1$-$C_3$-alkyl as mentioned above, especially methyl, $C_1$-$C_3$-alkoxy such as methoxy, ethoxy, propoxy and isopropoxy, especially methoxy, or halogen such as fluorine, chlorine, bromine and iodine, especially fluorine and chlorine; phenyl which can carry one to three of the following: $C_1$-$C_4$-alkyl as mentioned above, especially methyl, $C_1$-$C_4$-haloalkyl, especially trifluoromethyl, $C_1$-$C_4$-alkoxy as mentioned above, especially methoxy, $C_1$-$C_4$-haloalkoxy, especially trifluoromethoxy, halogen as mentioned above, especially fluorine and chlorine, nitro and cyano;

$R^2$ hydrogen; alkyl as mentioned for $R^1$, eg. $C_1$-$C_4$-alkyl, especially methyl and ethyl, cycloalkyl as mentioned for $R^1$, especially cyclohexyl, benzyl and $C_3$-$C_6$-alkenyl, especially allyl;

A $NR^3R^4$ where $R^3$ is hydrogen,
  alkyl, alkenyl or alkynyl such as $C_1$-$C_6$-alkyl, preferably $C_1$-$C_3$-alkyl as mentioned above, especially methyl, ethyl and isopropyl, $C_3$-$C_6$-alkenyl, especially $C_3$-$C_5$-alkenyl such as 2-propenyl, 1-methyl-2-propenyl and 1,1-dimethyl-2-propenyl, $C_3$-$C_6$-alkynyl, especially $C_3$-$C_5$-alkynyl such as 2-propynyl, 1-methyl-2-propynyl and 1,1-dimethyl-2-propynyl, $C_3$-$C_6$-cycloalkyl as mentioned above, especially cyclopropyl and $R^4$ is, for example, unsubstituted or substituted alkyl, alkenyl or alkynyl such as $C_1$-$C_6$-alkyl, especially $C_1$-$C_4$-alkyl such as methyl, ethyl, propyl, isopropyl, butyl, isobutyl, sec-butyl or tert-butyl, which can be substituted once by $C_1$-$C_4$-alkoxy such as methoxy, ethoxy, propoxy, isopropoxy, butoxy, isobutoxy, sec-butoxy or tert-butoxy, especially methoxy and ethoxy, $C_1$-$C_4$-alkylthio such as methylthio, ethylthio, propylthio, isopropylthio, butylthio, isobutylthio, sec-butylthio or tert-butylthio, especially methylthio and ethylthio, halogen as mentioned for $R^1$, especially fluorine and chlorine, $C_3$-$C_6$-cycloalkyl as mentioned for $R^1$, especially cyclopropyl, cyano or phenyl; $C_3$-$C_6$-alkenyl, especially $C_3$-$C_5$-alkenyl such as 2-propenyl, 1-methyl-2-propenyl or 1,1-dimethyl-2-propenyl, $C_3$-$C_6$-alkynyl, especially $C_3$-$C_5$-alkynyl such as 2-propynyl, 1-methyl-2-propynyl or 1,1-dimethyl-2-propynyl, a cycloaliphatic radical, eg. $C_3$-$C_6$-cycloalkyl as mentioned for $R^1$, especially cyclopropyl, cyclopentyl and cyclohexyl, which can be substituted up to twice by $C_1$-$C_4$-alkyl as mentioned above, especially methyl and ethyl, or halogen as mentioned for $R^1$, especially fluorine and chlorine;

phenyl which can carry one to three of the following: $C_1$-$C_4$-alkyl as mentioned for $R^1$, especially methyl, $C_1$-$C_4$-haloalkyl, especially trifluoromethyl, $C_1$-$C_4$-alkoxy, especially methoxy, halogen as mentioned for $R^1$, especially fluorine and chlorine, cyano or nitro, or $R^3$ and $R^4$ together form a methylene chain which has 4 to 7 members and can be interrupted by oxygen, sulfur or N-methyl, or A is $OR^5$ where $R^5$ is $C_1$-$C_4$-alkyl as mentioned for $R^1$, especially methyl and ethyl, $C_3$-$C_6$-cycloalkyl as mentioned for $R^1$, especially cyclohexyl, benzyl and $C_3$-$C_6$-alkenyl, especially allyl.

The β-keto acids and β-keto esters II required for the process according to the invention either are commercially available or can be prepared by conventional processes (eg. Org. Synth., 61 (1982) 5; Org. Synth. Coll. Vol. 4 (1963) 415; J. Org. Chem., 44 (1979) 310; J. Org. Chem., 43 (1978) 2087; Synthesis (1978) 829; Org. Prep. Proced Int. 10 (1978) 221).

The hydroximyl chlorides IIIb are disclosed in the literature (cf., for example, DE-A1-28 17 838; J. Org. Chem., Vol 48 (1983); U.S. Pat. No. 3,557,190).

The hydroximyl chlorides IIIa can be prepared, for example, by the process described in DE-B 19 63 061 starting from acetoacetamides. It is possible in principle to use this general process also to prepare hydroximyl chlorides which have not to date been described in the literature. One example is described hereinafter.

EXAMPLES

Preparation of hydroximyl chlorides IIIa Cyclopropylcarbamoylformhydroximyl chloride

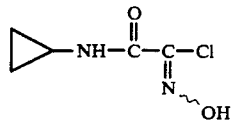

42.0 g (0.5 mol) of diketene are added dropwise to a mixture of 28.5 g (0.5 mol) of cyclopropylamine and 500 ml of water at room temperature. During this, the pH falls from 12.0 to 5.5–6.5. The mixture is then stirred for 10 min, 37.9 g (0.55 mol) of sodium nitrite are added and subsequently about 75 ml of concentrated hydrochloric acid are added in such a way that the pH always remains above 4.5. After the addition is complete, 41.1 g (0.58 mol) of gaseous chlorine are passed in at room temperature. The reaction is checked for completion by TLC or HPLC. The hydroximyl chloride produced in the reaction can be isolated either by filtration at 0° C. or by extraction several times with 200 ml of ethyl acetate each time and removal of the solvent under reduced pressure. The resulting solid is washed with water and dried not above 40° C. under reduced pressure. 72.1 g (89%) of cyclopropylcarbamoylformhydroximyl chloride are obtained as a white solid.

$^1$H-NMR (250 MHz, DMSO): δ=0.50–0.78 (m; 4H), 2.75 (m; 1H), 8.48 (d; 1H, NH), 12.80 (s; 1H, OH)

General method for preparing 3-carbamoylisoxazole-4-carboxylic esters Ia by reacting β-keto esters IIa with hydroximyl chlorides IIIa in the presence of magnesium alcoholates.

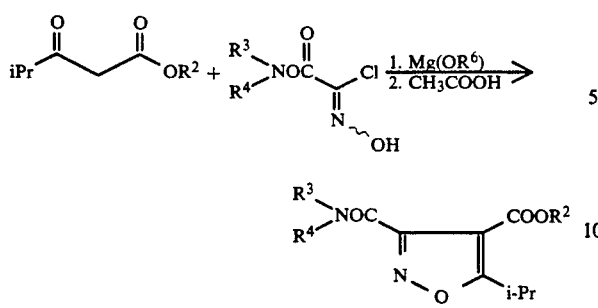

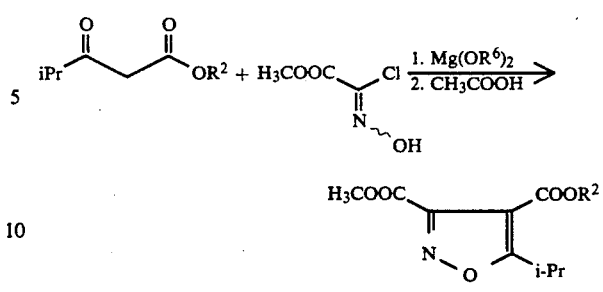

$R^2 = R^6 =$ methyl or ethyl 0.31 mol of magnesium turnings is reacted with 50 ml of dry alcohol ($R^6OH$) with exclusion of moisture. The reaction is started by adding a few drops of bromine or tetrachloromethane or a spatula-tip of iodine. After the reaction is complete, the excess alcohol is removed under reduced pressure. The resulting magnesium alcoholate is suspended in 400 ml of a dry inert organic solvent and subsequently 0.3 mol of $\beta$-keto ester II in 50 ml of solvent is added dropwise at 10°-20° C. The mixture is stirred at room temperature for about 3 h. 0.3 mol of hydroximyl chloride IIIa in 300 ml of dry inert organic solvent is slowly added to the resulting solution of magnesium enolate at room temperature over the course of 5 hours. The mixture is then stirred at room temperature for 4–12 h, acidified by adding about 45 g of acetic acid and then refluxed for 1–4 h. Completion of the cyclization is checked by HPLC. The reaction mixture is allowed to cool and taken up in a mixture of water and ethyl acetate, the phases are separated, the aqueous phase is extracted with ethyl acetate, the combined organic phases are dried, and the solvents are stripped off in a rotary evaporator. If necessary, the resulting crude product is purified by filtration through a silica gel column (cyclohexane/ethyl acetate).

$R^2 = R^6 =$ methyl or ethyl 0.3 mol of $\beta$-keto ester IIa is added to a solution of 0.31 mol of commercially available magnesium methylate or ethylate in 400 ml of dry inert organic solvent at 10°-20° C. The mixture is stirred at room temperature for about 3 h. 0.3 mol of hydroximyl chloride IIIb in 300 ml of dry inert organic solvent is added to the resulting solution of magnesium enolate at room temperature over the course of 5 hours. The mixture is then stirred at room temperature for 4–12 h, acidified by adding 45 g of acetic acid, and refluxed for 1–4 h and then further treated as described above.

TABLE 2

Preparation of isoxazole-3,4-dicarboxylic esters Ib with $R^5 = CH_3$ and $R^1 =$ i-propyl

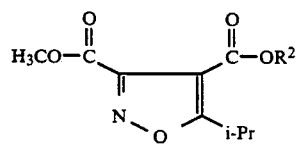

| Example | $R^2$ | Solvent | Yield (%) | $^1$H-NMR (CDCl$_3$; 250 MHz) δ in ppm |
|---|---|---|---|---|
| 2a | Me | THF | 74 | 1.38(d, 6H); 3.76(sp, 1H); 3.87(s, 3H); 3.99(s, 3H) |
| 2b | Et | THF | 78 | 1.34(t, 3H); 1.37(d, 6H); 3.73(sp, 1H); 4.00(s, 3H); 4.29(1, 2H) |
| 2c | Et | Toluene | 69 | 1.34(t, 3H); 1.37(d, 6H); 3.73(sp, |

TABLE 1

Preparation of 3-carbamoylisoxazole-4-carboxylic esters

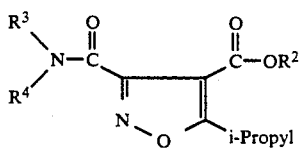

| Example | $R^2$ | $R^3$ | $R^4$ | Solvent | Yield (%) | $^1$H-NMR (CDCl$_3$; 250 MHz) δ in ppm |
|---|---|---|---|---|---|---|
| 1a | Me | H | cyclo-Pr | THF | 80 | 0.60–0.93(m, 4H); 1.36(d, 6H); 2.92(m, 1H); 3.70(sp, 1H); 3.89(s, 3H); 7.84(bs, 1H, NH) |
| 1b | Et | H | cyclo-Pr | THF | 83 | 0.60–0.90(m, 4H); 1.36(d, 6H); 1.37(t, 3H); 2.93(m, 1H); 3.73(sp, 1H); 4.35(q, 2H); 7.75(bs, 1H, NH) |
| 1c | Et | H | cyclo-Pr | Toluene | 74 | 0.60–0.90(m, 4H); 1.36(d, 6H); 1.37(t, 3H); 2.93(m, 1H); 3.73(sp, 1H); 4.35(q, 2H); 7.75(bs, 1H, NH) |
| 1d | Et | H | tert-Bu | Toluene | 79 | 1.36(d, 6H); 1.37(t, 3H); 1.48(s, 9H); 3.72(sp, 1H); 4.35(q, 2H); 7.00(bs, 1H, NH) |
| 1e | Et | H | tert-Bu | THF | 84 | 1.36(d, 6H); 1.37(t, 3H); 1.48(s, 9H); 3.72(sp, 1H); 4.35(q, 2H); 7.00(bs, 1H, NH) |
| 1f | Me | Me | Me | THF | 85 | 1.38(d, 6H); 2.95(s, 3H); 3.16(s, 3H); 3.84(sp, 1H); 3.85(s, 3H) |
| 1g | Me | H | i-Pr | THF | 83 | 1.28(d, 6H); 1.36(d, 6H); 3.72(sp, 1H); 3.88(s, 3H); 4.28(m, 1H); 7.28(d, 1H, NH) |

Me = methyl, Et = ethyl, Pr = propyl, Bu = butyl, THF = tetrahydrofuran

General method for preparing isoxazole-3,4-dicarboxylic esters Ib by reacting $\beta$-keto esters IIa with hydroximyl chlorides IIIb in the presence of magnesium alcoholates.

TABLE 2-continued

Preparation of isoxazole-3,4-dicarboxylic esters Ib with $R^5 = CH_3$ and $R^1 = $ i-propyl

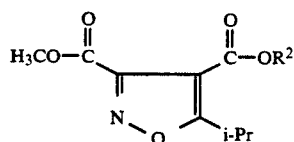

| Example | $R^2$ | Solvent | Yield (%) | $^1$H-NMR (CDCl$_3$; 250 MHz) δ in ppm |
|---|---|---|---|---|
| | | | | 1H); 4.00(s, 3H); 4.29(t, 2H) |

COMPARATIVE EXAMPLES

EXAMPLE I

Dimethyl 5-methylisoxazole-3,4-dicarboxylate 23.2 g (0.2 mol) of methyl acetoacetate in 50 ml of absolute methanol are added to a solution of 10.8 g (0.2 mol) of sodium methylate (cryst.) in 150 ml of dry methanol at 0°–10° C., and the mixture is stirred at this temperature for 3 h. Subsequently, at 0°–10° C., 27.5 g (0.2 mol) of methyl α-chloro-α-hydroximinoacetate in 100 ml of absolute methanol are slowly added dropwise, and the mixture is stirred at room temperature for 12 h. The solution is worked up by evaporation to a small volume and addition of 800 ml of water, when the product separates out as oil. The organic phase is separated off, the aqueous phase is extracted with dichloromethane, the combined organic phases are dried, and the solvent is stripped off in a rotary evaporator. The residue is purified by column chromatography on silica gel (solvent cyclohexane/ethyl acetate 3:1). 15.1 g (38% of theory) of dimethyl 5-methylisoxazole-3,4-dicarboxylate are obtained.

$^1$H-NMR (250 MHz; CDCl$_3$) d=2.72 (s;3H), 3.87 (s;3H), 4.00 (s;3H)

EXAMPLE II 0.3 mol of β-keto ester in 100 ml of solvent is added dropwise to 9.9 g (0.33 mol) of sodium hydride (100%) in 500 ml of dry toluene or benzene at room temperature, and the mixture is stirred for 3 h. Subsequently 0.3 mol of methyl α-chloro-α-hydroximinoacetate in 200 ml of solvent is added, and the mixture is stirred at room temperature for 12 h and subsequently transferred into a Soxhlet apparatus (extraction thimble filled with 4 Å molecular sieve), 3 g of methanesulfonic acid are added, and the mixture is refluxed for 1–4 h. It is allowed to cool, the organic phase is washed once with water, and the solvent is stripped off under reduced pressure. If required, the crude product is purified by filtration through a silica gel column (solvent cyclohexane/ethyl acetate). The results of the various experiments are detailed in Table 3.

TABLE 3

Comparative Examples

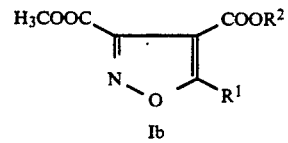

Ib

| $R^1$ | $R^2$ | Solvent | Yield (%) | $^1$H-NMR (CDCl$_3$; 250 MHz) δ in ppm |
|---|---|---|---|---|
| Me | Et | Toluene | 63 | cf. DE-A 39 31 627; page 163 |
| Me | Me | Benzene | 48 | 2.70(s, 3H); 3.88(s, 3H); 3.98(s, 3H) |
| Me | Me | Toluene | 46 | 2.70(s, 3H); 3.88(s, 3H); 3.98(s, 3H) |
| Et | Me | Toluene | 21 | 1.36(t, 3H); 3.12(q, 2H); 3.87(s, 3H); 3.99(s, 3H) |
| iPr | Me | Toluene | 31 | 1.38(d, 6H); 3.76(sp, 1H); 3.87(s, 3H); 3.99(s, 3H) |
| iPr | Me | Benzene | 28 | 1.38(d, 6H); 3.76(sp, 1H); 3.87(s, 3H); 3.99(s, 3H) |
| iPr | Et | Toluene | 32 | 1.34(t, 3H); 1.37(d, 6H); 3.73(sp, 1H); 4.00(s, 3H); 4.29(q, 2H) |

We claim:
1. A process for preparing isoxazole-3,4-dicarboxylic acid derivatives of the formula I

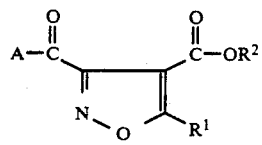

where
- $R^1$ is hydrogen, alkyl, cycloalkyl or phenyl, or a 5- to 6-membered heterocyclic radical, and the organic radicals can have substituents which are inert under the reaction conditions;
- $R^2$ is hydrogen, alkyl, cycloalkyl, benzyl or $C_3$-$C_6$-alkenyl;
- A is $NR^3R^4$ where $R^3$ is hydrogen or an aliphatic or cycloaliphatic radical and $R^4$ is an aliphatic or cycloaliphatic radical or unsubstituted or substituted phenyl, or $R^3$ forms together with $R^4$ a 4- to 7-membered alkylene chain which can be interrupted by oxygen, sulfur or N-methyl, or
- is $OR^5$ where $R^5$ is alkyl, cycloalkyl, benzyl or alkenyl;

by deprotonation of a CH-acid compound of the formula II

using a base and reacting with hydroximyl chlorides of the formula III

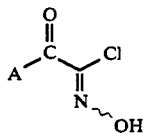

III wherein a magnesium alcoholate of the formula IV $$Mg(OR^6)_2 \quad \text{IV}$$

where $R^6$ is an aliphatic or cycloaliphatic radical is used for the deprotonation.

2. A process as claimed in claim 1, wherein magnesium methylate or magnesium ethylate is used as base.

3. A process as claimed in claim 1, wherein the base is used in an amount of from 1 to 5 mol per mol of β-keto ester II ($R^2 \neq H$) or from 2 to 5 mol per mol of β-keto acid II ($R^2 = H$).

4. A process as claimed in claim 1, wherein the reaction is carried out in the presence of an aromatic hydrocarbon or of an ether as solvent.

5. A process as claimed in claim 4, wherein toluene or tetrahydrofuran is used as solvent.

* * * * *